US006477233B1

(12) United States Patent
Ribbing et al.

(10) Patent No.: US 6,477,233 B1
(45) Date of Patent: Nov. 5, 2002

(54) MINIATURE X-RAY SOURCE

(75) Inventors: Carolina Ribbing, Uppsala; Pelle Rangsten, Storvreta; Lars Tenerz, Uppsala; Leif Smith, Uppsala; Klas Hjort, Uppsala, all of (SE)

(73) Assignee: Radi Medical Technologies AB, Uppsala (SE)

( * ) Notice: Subject to any disclaimer, the term of this patent is extended or adjusted under 35 U.S.C. 154(b) by 28 days.

(21) Appl. No.: 09/585,283

(22) Filed: Jun. 2, 2000

Related U.S. Application Data
(60) Provisional application No. 60/137,478, filed on Jun. 4, 1999.

(51) Int. Cl.[7] .............................................. H01J 35/06
(52) U.S. Cl. ...................... 378/136; 375/119; 375/121; 375/122; 375/129
(58) Field of Search ....................... 378/136, 64, 65, 378/68, 119, 121, 122, 129

(56) References Cited

U.S. PATENT DOCUMENTS

| | | | | |
|---|---|---|---|---|
| 3,714,486 A | * | 1/1973 | McCrary | 313/55 |
| 5,258,685 A | * | 11/1993 | Jaskie et al. | 313/309 |
| 5,854,822 A | | 12/1998 | Chornenky et al. | 378/122 |
| 6,204,595 B1 | * | 3/2001 | Falabella | 313/308 |

FOREIGN PATENT DOCUMENTS

| | | |
|---|---|---|
| WO | WO 98/36796 | 8/1998 |
| WO | WO 98/48899 | 11/1998 |
| WO | WO 99/00816 | 1/1999 |

OTHER PUBLICATIONS

Rangsten, et al., "Field Emitting Structures Intended for a Miniature X–Ray Source", Sensors & Actuators A82, pp. 24–29 (May 2000), ISSN 0924–4247.

Rangsten, et al., "Field Emitting Structures Intended for a Miniature X–Ray Source", Proc. of the 10th Int. Conf. On Solid–State Sensors and Actuators (Transducers '99), Sendai, Japan, (Jun. 1999).

Ransten, et al., "Diamond Membrane Based Miniature X–Ray Source", 10th European Conf. On Diamond, Diamond–Like Materials, Carbon Nanotubes, Nitrides & Silicon Carbide, (Diamond 1999) Prague,.Czech Republic (Sep. 1999).

Rangsten, et al. "Microstructure Technology in Silicon, Quartz, and Diamond", Acta Universitatis Upsaliensis Comprehensive Summaries of Uppsala Disssertations from the Faculty of Science and Technology 484 p. 37 (Nov. 1999) ISBN 91–554–4572–1.

* cited by examiner

*Primary Examiner*—Robert H. Kim
*Assistant Examiner*—Courtney Thomas
(74) *Attorney, Agent, or Firm*—Foley & Lardner

(57) ABSTRACT

An X-ray source includes a first support member and a second support member joined together so as to form a cavity between them and such that they are electrically insulated from each other. A cathode and an anode are located inside the cavity and opposite each other. The cathode is suitably made of diamond or diamond like material, and includes at least one pointed element.

4 Claims, 6 Drawing Sheets

MINIATURE X-RAY SOURCE

The Applicants hereby claim the benefit of prior United States Provisional Application No. 60/137,478, filed Jun. 4, 1999 (on which this present application is based). The entire contents of this 60/137,478 application are incorporated herein by reference.

The present invention relates to generation of X-rays for medical purposes, and in particular it relates to miniature X-ray source for intravascular treatment of lesions in body tissue, in particular for treatment of stenosis in coronary vessels and treatment of cancer tumors.

BACKGROUND OF THE INVENTION

Radiation therapy is a well-established method for treatment of several diseases, including cancer. The presumptive usefulness of a miniature X-ray source is clear. The insertion of such a source into vessels or other body cavities would allow the delivered dose to be confined to a small tissue region. More specific, a catheter with a miniaturized X-ray source could be used for irradiation of cardiovascular tissue. A stenosed coronary artery is often treated by balloon dilatation, i.e. Percutaneous Transluminal Coronary Angioplasty (PTCA). A small balloon at the top of a plastic catheter is inserted into the femoral artery, guided in the vessels to the site of stenosis, and inflated. As the stenosis is pushed out by the balloon the artery is widened to normal inner diameter. However, in about one third of the patients a restenosis will occur after the PTCA. One means of reducing the restenosis rate is to treat the vessel wall locally with gamma or beta radiation in conjunction with the PTCA. An absorbed dose of about 10–50 Gy from catheterised gamma and beta sources has been shown to lower the restenosis rate substantially in several trials.

In contrast to radioactive sources the here suggested X-ray source would be switchable on and off electronically. Furthermore, the energy of its radiation would be given by the voltage between the electrodes. As the range of X-rays in tissue depends on the X-ray energy the optimal range could be obtained by applying the corresponding electrode voltage.

In applicants own U.S. patent application Ser. No. 08/805,296 (corresponding to WO 98/36796), incorporated herein in its entirety by reference, there is disclosed a miniaturized source If ionizing electromagnetic radiation, comprising a pair of plates; a hermetically sealed microcaoity formed in one of the plates; a pair of electrodes in the form of a cathode and an anode, at least one electrode being located in the microcavity and the other electrode being located on the other plate; the anode being at least partly of a metal having a relatively high atomic weight; and electrically conducting leads connected to the cathode and the anode.

The cathode of the above device is preferably provided as a pointed tip of a material such as oxides of metals from group II in the periodic table, including cesium, barium and magnesium.

Although representing a major step forward in the art of radiation sources, the disclosed device has certain shortcomings.

In view of the cathode being shaped as a pointed tip the current density attainable will not be very high, and hence the number of electrons impinging on the anode will be relatively small, and thus the generated X-ray intensity will not be very high. In a therapy situation this would lead to longer treatment times, which is undesirable.

U.S. Pat. No. 5,854,822 discloses an X-ray device having a cold cathode. The cathode is composed of a mixture of a diamond powder and a getter, and has the general shape of a rotationally symmetrical cone. This patent specifically discloses that diamond powder based cathodes yield better performance that diamond coated cathodes.

WO 98/48899 discloses the use of microscopic metal tips, such as of Mo, together with a gate electrode for the purpose of controlling the electron emission. Thereby high fields are achieved locally. In addition a specific X-ray transmission window is used in order to achieve sufficiently short treatment times. The provision of a gate electrode and the addition of a specific X-ray transmission window adds to the complexity of the structure, which is cumbersome and expensive considering the small dimensions. In particular the contacting and electrical control of the gates is difficult.

SUMMARY OF THE INVENTION

Thus, there exists a need for miniaturized radiation devices for therapeutic applications, which are capable of generating X-ray radiation of an intensity of a desired magnitude.

Therefore the object of the present invention is to improve the prior art devices in order to meet the above requirements.

This object is achieved with a miniaturized X-ray radiation source as defined in claim 1.

Thereby the cathode is provided as a layer comprising diamond or carbon based material having diamond like structure and exhibiting a plurality of tips. Examples are polycrystalline diamond, diamond like material (by which we i.a. mean boron nitride and silicon carbide, and other structurally similar materials), amorphous diamond and diamond like carbon. The layer can be deposited onto a suitable substrate, having the desired geometry.

The tips may be formed by depositing a continuous/covering polycrystalline layer of diamond, in which case they will be in the nanometer range, or they may be made by depositing diamond in recesses made by an isotropic etching in single crystal silicon to provide "templates" for pyramidally shaped tips. Once the diamond is deposited in said recesses, enough of the matrix silicon is etched away to leave the pyramids exposed, extending but from the silicon base. It is also possible to employ isotropic etching, whereby the shape of the tips will be more quasi-spheroidal or egg-shaped.

BRIEF DESCRIPTION OF THE DRAWINGS

The invention will be described below with reference to the attached drawings in which

FIG. 3 shows an alternative to the embodiment of FIG. 1a;

DETAILED DESCRIPTION OF PREFERRED EMBODIMENTS

Figure 1:
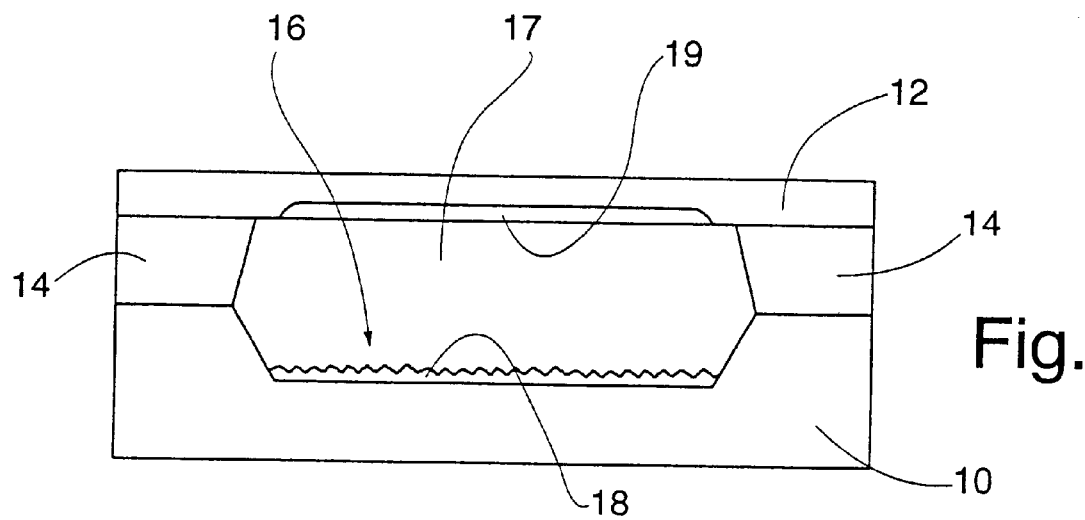
FIG. 1a shows a first embodiment of the invention.

The principle for a miniature X-ray source according to a first embodiment of the invention is shown schematically in FIG. 1.

It comprises a base element 10 and a cover element 12 connected to the base 10 via an insulating member 14. The base element 10 can be made of Si or other semiconductor material, glass, ceramic materials or metal, and has a depression 16 formed therein. Thereby a cavity 17 is formed between said base element 10 and said cover 12. The cover can be made of e.g. Si or other semiconductor material, glass, ceramic materials or metal, or of a combination of metal/semiconductor. The cavity is evacuated.

The depression has a flat bottom, and on the bottom of the depression a field emitting cathode 18 is provided in the form of a continuous layer of a suitable material, which preferably is diamond, and comprises a large number of micro-tips. In the cover an anode 19 is provided, arranged opposite to the cathode. Thus, if a voltage of appropriate magnitude is applied between the anode and the cathode, electrons will be emitted from the cathode and accelerated towards the anode. The electrons are accelerated in the electrical field and will impact on the anode. On impact their kinetic energy will be transformed into heat and radiation; characteristic radiation and Bremsstrahlung. It is generally known that anodes made of materials of high atomic numbers such as W,Au,Pt, Ir, etc. are more efficient as X-ray emitters as compared to elements with low atomic numbers.

This embodiment is referred to as a vertical structure.

Figure 2:
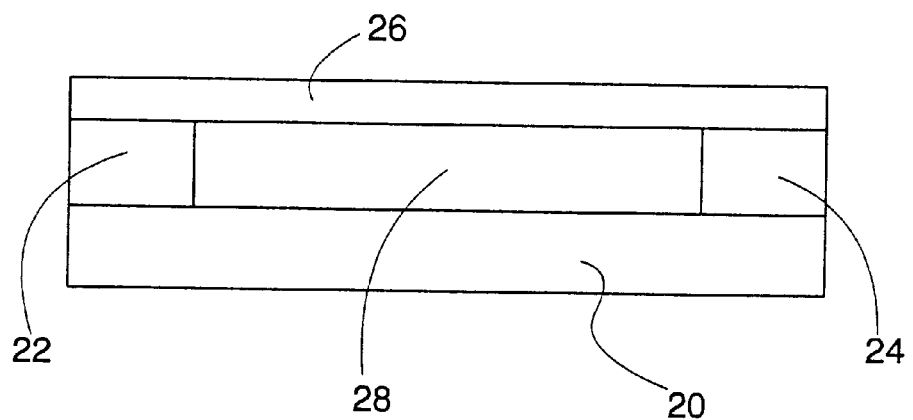
FIG. 2a shows a second embodiment of the invention.

An alternative principle according to a second embodiment of the invention is shown schematically in FIG. 2a.

Here, the device also comprises a base element 20. However, in this case the base element is an insulator, and has both a cathode 22 and an anode 24 provided on its surface. On top of this structure a second insulator element 26 is provided so as to form a sandwich structure of the base 20 add the cover 26. Around the circumference, or at the edges between the base and cover insulating elements are provided so as to form an enclosure in which the anode and cathode is located. Thus, a cavity is 28 formed between cover and base, and this cavity is evacuated. If an appropriate voltage is applied between anode and cathode, electron will be accelerated towards the anode and the direction of electron emission will in this case be parallel to the plane of the base element.

This embodiment is referred to as a lateral structure.

Now preferred embodiments of the vertical and lateral structures, respectively, will be discussed in detail.

The embodiment disclosed in FIG. 1a can be realized in various ways. It is in a first aspect possible to make a device that has essentially the schematically shown structure.

However, due to the material thickness of the base 10 and the cover 12 respectively, there will inevitably be some intensity losses because of absorption and/or scattering primarily in the cover material. In order to maximize the intensity in the therapeutic radiation, it would thus be desirable to make this part of the device as thin as possible. However, the material in the base and cover could also be used to advantage for filtering purposes. Assume that one wishes to provide essentially only a characteristic peak at say 10 keV. Then the Bremsstrahlung below that value could be cut off by suitable selection of thickness and/or material in the cover and/or the base.

Furthermore, as indicated in the background, a single cathode in the form of a pointed tip will not generate enough field emission current to provide as high a radiation intensity as desired. Therefore the cathode is provided as a plurality of micro-tips. Thereby the overall current density can be increased, and hence the overall X-ray intensity. The methods of making the device and in particular the micro-tips will be discussed more in detail below.

Figure 3:
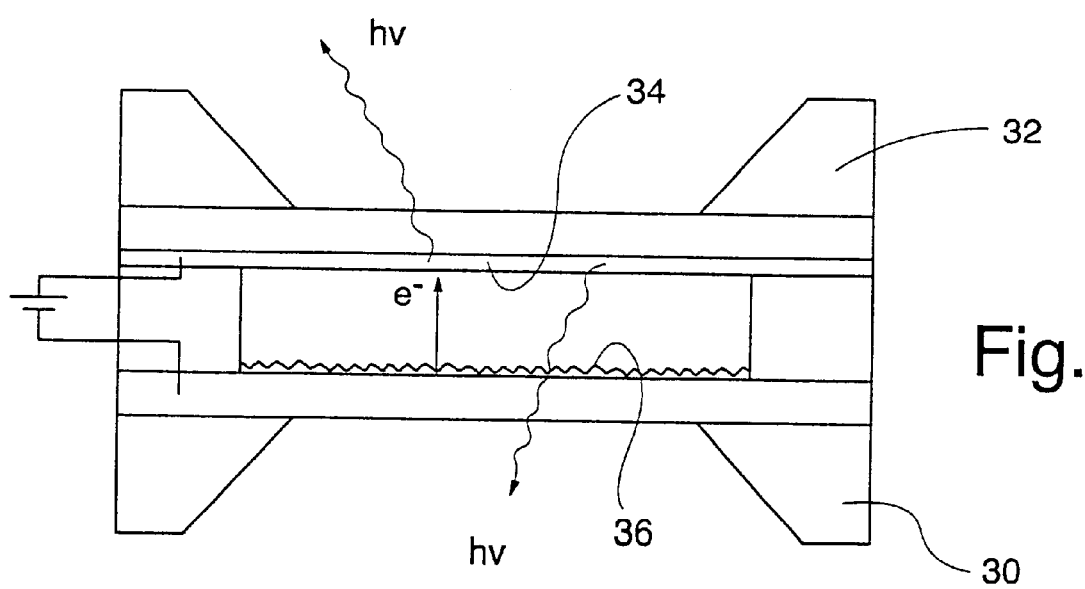

In FIG. 3 there is shown an alternative embodiment wherein preferably all material of the base 30 and cover 32 elements has been removed from the back side of the anode 34 and the cathode 36, respectively. Thereby the anode and cathode can be characterized as self supporting membranes, within a rigid frame structure surrounding the membranes, the frame being comprised of the remaining portions of the base and the cover respectively.

Figure 4:
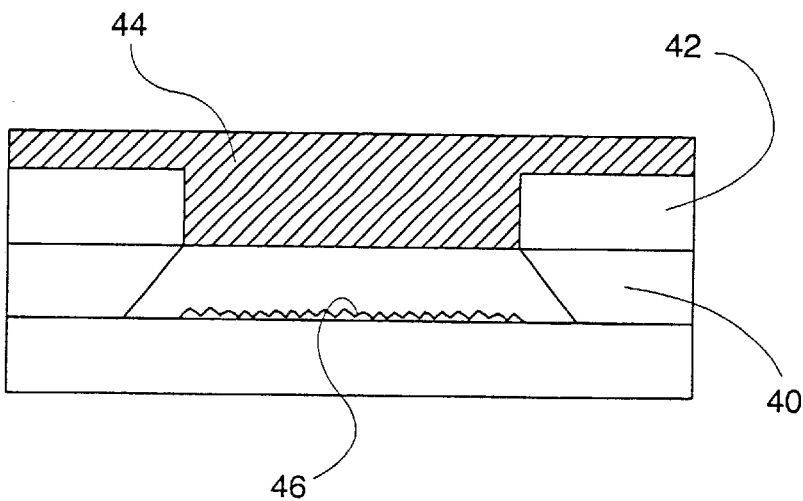
FIG. 4 illustrates still another variation of the first embodiment.

In FIG. 4 a variation of the embodiment in FIG. 1 is shown. The base element 40 is similar to that of FIG. 1, but in the cover element 42 a central hole has been made. This hole has been filled with anode material 44 by deposition, and also a portion of the upper surface of the cover element 42 is covered by the anode material. This upper portion will provide an appropriate contact surface for the connection to an external power source.

Figure 5:
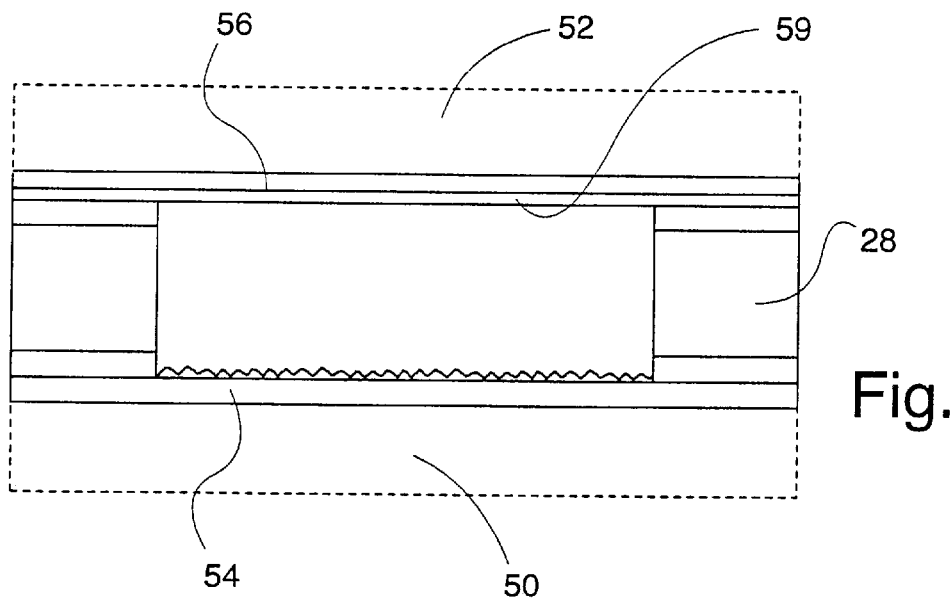
FIG. 5 illustrates a further variation of the first embodiment.

In FIG. 5 an alternative embodiment is shown. This is essentially identical to the embodiment of FIG. 3, but here the entire base 50 and cover 52 structures have been removed (removed material indicated with broken lines), such that the diamond membranes 54, 56 themselves will function as base and cover, separated by insulating material 58. The membrane that has the function of the anode will of course have a layer 59 of a suitable metal with high atomic number as discussed above, deposited thereon. This embodiment will of course be weaker than the embodiment of FIG. 3, but on the other hand it will be thinner, which is advantageous in certain cases, where the space available may be small.

Figure 6:
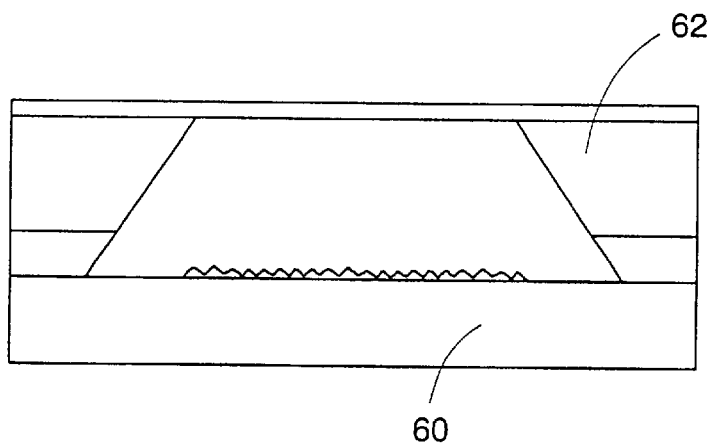
FIG. 6 shows a still further variation of the first embodiment.

In FIG. 6 still another embodiment is shown. Here the cavity formed between base and cover 60 and 62 respectively, is made by providing a recessed cover and attaching a flat base member thereto, which is an inverted version of the embodiment of FIG. 1a.

In all the embodiments of FIGS. 1 to 6, the cathode is made of polycrystalline or amorphous diamond, deposited e.g. by HFCVD (Hot Filament Chemical Vapor Deposition). This will give a structure of the surface comprising many very small pointed tips of diamond, which is essential to the function of the device. A preferred composition of the cathode is boron doped polycrystalline diamond, in the form of a thin film. The thickness of the film could be about 20 $\mu$m, although other thicknesses are possible, and may be selected according to the specific requirements of a certain application.

The anode is also made of boron doped polycrystalline diamond, in the form of a thin film by HFCVD. However, on the surface of the anode a thin layer of a metal is deposited. Suitable metals are Ni and Cu, but other metals are conceivable such as W, Au and the like.

As indicated schematically by arrows in FIG. 3 (although of course the same situation is relevant for all embodiments), X-rays (characteristic radiation) will be emitted in all directions, and since the diamond membranes are transparent to X-rays, they will not cause intensity losses.

An entire assembly according to the invention, in the following referred to as a "radiation chip", can be made in the following way (reference is made to the embodiment of FIG. 4, but the principle can be applied to all embodiments).

Figure 7A:
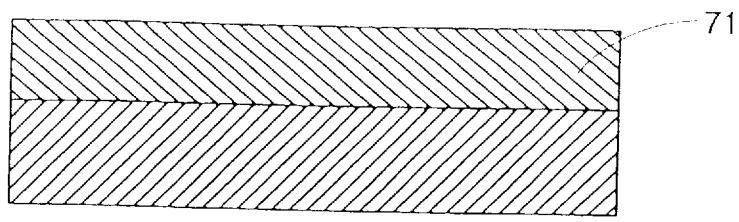
FIGS. 7a–7e shows a sequence of manufacturing steps for making the embodiment of FIG. 4.
Figure 7B:
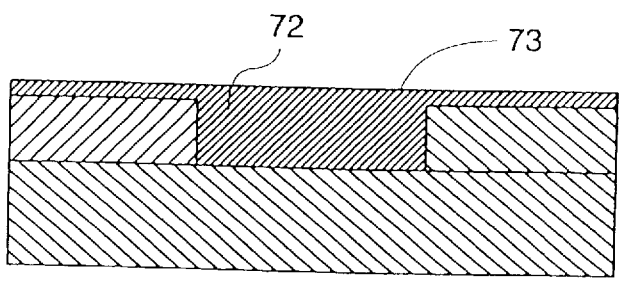
Figure 7C:
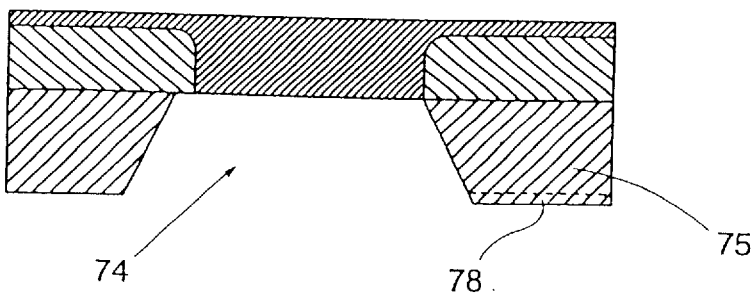
Figure 7D:
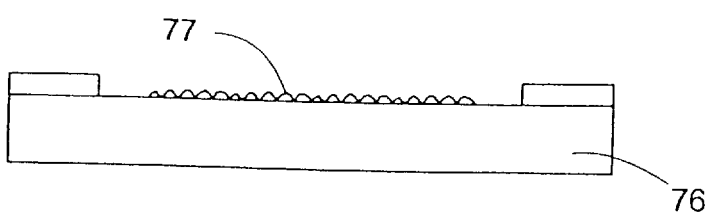

A silicon wafer 70 is oxidized to provide a layer of insulation silicon dioxide 71 (FIG. 7a). By lithographic techniques a mask (not shown) is provided on the oxide and an opening 72 is etched through the oxide down to the silicon. Then the opening and the top surface is (at least partially) covered by deposition with an anode material 73 (FIG. 7b). In a subsequent step the silicon wafer is masked and an opening 74 in the silicon is etched so as to expose the anode material through said silicon wafer (FIG. 7c). The portion of the silicon wafer that remains after etching, ill function as a spacer element 75 to provide the cavity inside the finished assembly. This unit will be referred to as the cover element.

A base element 76, e.g. made of silicon, is provided with a polycrystalline diamond film 77, and the base element and the cover element are joined e.g. by bonding to provide the finished radiation chips Before joining the two elements (base and cover), evacuation channels 78 are made in one surface, e.g. the bottom surface of the spacer part 75 of the cover element. This enables the cavity formed between the halves to be evacuated. The preferred vacuum level is between $10^{-4}$ and $10^{-9}$ torr. The channels are then sealed by conventional techniques, well known to &e skilled person.

Figure 7E:
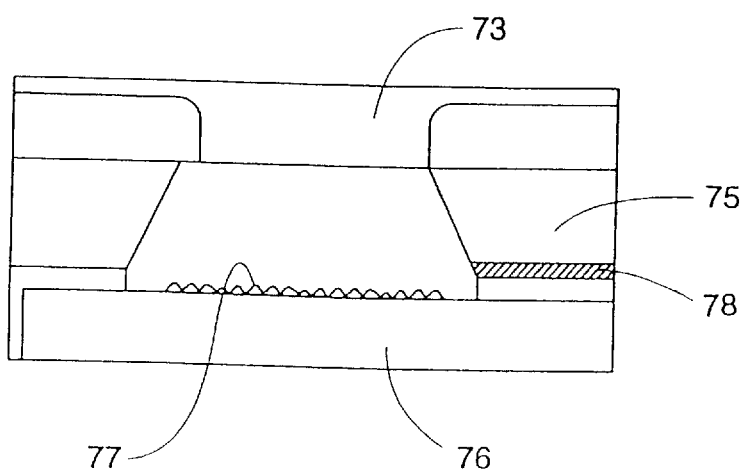

The assembled unit is shown in FIG. 7e. It comprises the base 76, a cathode made of polycrystalline or amorphous diamond 77, spacer portions 75, anode 73, and an evacuated cavity. The evacuation channel 78 is shown to be sealed off.

Figure 8:
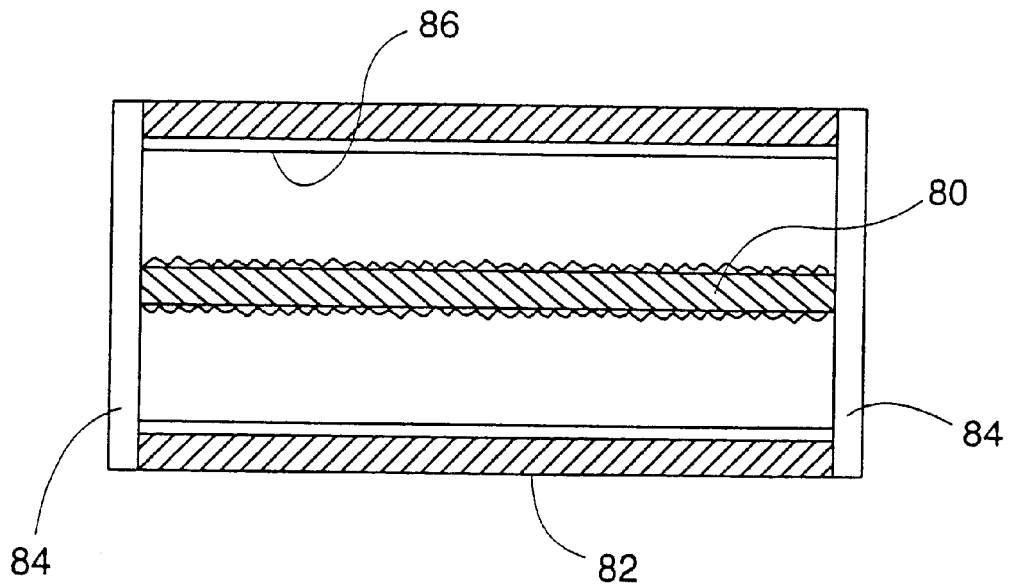
FIG. 8 is a cross section through a cylindrical variant of the device according to the invention.
Figure 9:
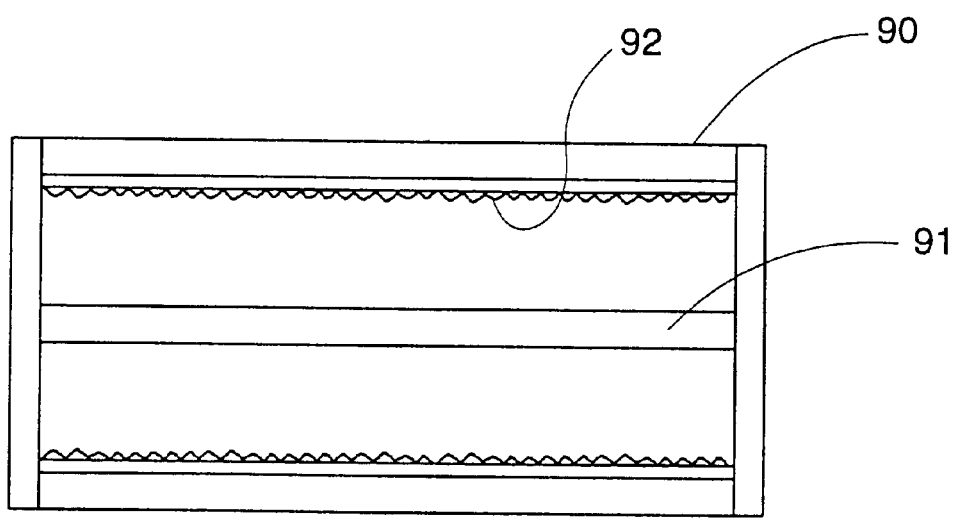
FIG. 9 illustrates a variation of the embodiment of FIG. 8.

In a third variation of the invention, the radiation source is made in a cylindrical geometry, illustrated in FIGS. 8 and 9.

In FIG. 8, which is a longitudinal cross section, the shown radiation source comprises a thin elongated member, such as a rod or even a wire 80. This member acts as a support for a thin film cathode, made of polycrystalline or amorphous diamond, having a surface structure of a plurality of very small pointed tips. Although shown to cover the entire surface of the rod or wire, the thin diamond film could be only partly covering the surface. This could be necessary or desirably in order to control the emission, and obtain exactly the desired distribution and intensity.

Around the centrally arranged rod or wire a cylindrical member 82 is provided. The cylinder is hermetically sealed by a cover element 84 at both ends, these cover elements also functioning as support members for the rod 80. The cylinder can be made of glass, having its interior surface 86 covered with anode material, such as Cu or Ni, but W or Au or the like can be used.

Also the anode material can be only partially covering the inner surface, e.g. by depositing a mesh like structure. In fact it is also possible to have an actual metal net made and to insert it inside the cylinder in close proximity to the inner wall of the cylinder.

FIG. 9 illustrates an inverted embodiment, wherein the central rod 91 is made of anode material, and the inner surface 92 of the cylinder 90 is covered with diamond film to provide the cathode.

Diamond has certain very beneficial properties making it especially suitable for use in this invention. IN the first place it has a low work function. It is an extremely good insulator in the undoped state, but can be made conductive by doping e.g. with boron. It has extremely low permeability for gas diffusion. Due to the latter property it is possible to encapsulate an entire assembly as disclosed in the description of embodiments above, using diamond. Thereby a hermetic sealing will be obtained that has excellent properties. Furthermore, diamond has excellent thermal conduction properties.

As indicated by providing the diamond as a thin film of polycrystalline or amorphous material, al surface may be obtained exhibiting a large number of very small pointed tips.

It is also possible to make pointed tips having a more controlled shape, and having a larger size. This may be achieved as follows (reference is made to FIGS. 10a to 10g), which is a description of one method. Of course any method capable of creating these shapes would be suitable.

Figure 10A:
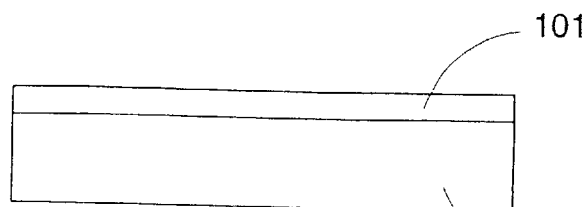
FIGS. 10a–10g illustrate manufacturing of pointed cathodes.
Figure 10B:
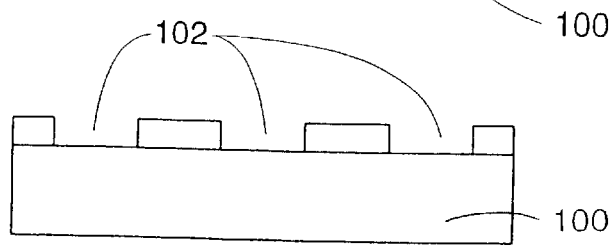
Figure 10C:
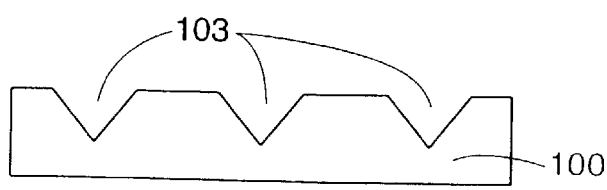
Figure 10D:
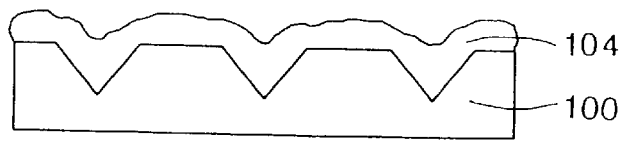
Figure 10E:
Figure 10F:
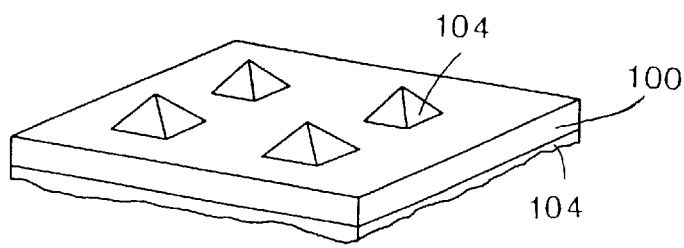
Figure 10G:
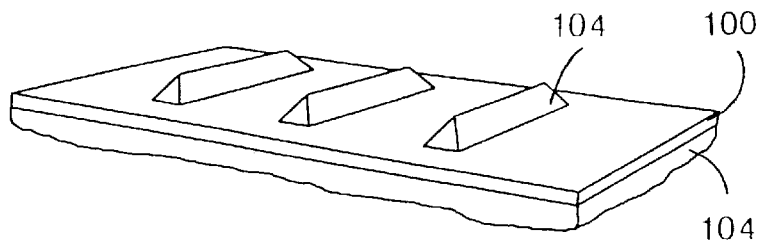

A silicon substrate 100 is oxidized to provide an oxide layer 101. Square openings 102 are made in the oxide. Using KOH or some other an isotropic etchant, so called 111-pits 103 are made in tho silicon, and the masking oxide is then removed. These pits will have pyramid like geometry. Diamond or diamond like material (polycrystalline or amorphous), preferably boron doped diamond is then deposited over the surface containing the pits 103. After deposition of the diamond, silicon is etched away from the other side of the aggregate, to expose the Pyramids, such that they protrude slightly from the surrounding silicon substrate. In FIG. 10f perspective view of the final structure is shown.

The openings need not be square but could have other shapes as well, such as circular, triangular, hexagonal etc.

Alternatively, instead of making square openings, one can make openings having a large aspect ratio, such as rectangular or even ellipsoid shape. Using the same procedure as described above, the result will be a plurality of wedge shaped ridges, protruding from a silicon substrate, see FIG. 10g.

By employing an isotropic etching procedure, the shape of the tips can be controlled to be quasi-spheroidal or egg-shaped. By "quasi-spheroidal" we mean a shape that is dome-like or arched, but not necessarily strictly conforming to the geometry of a sphere. This approach would employ methods well known to the skilled person and will not be further discussed herein.

The size of these structures can be controlled by the lithographic technique used. The tips cannot be made as small as the ones produced by the deposition of diamond directly onto a surface, but on the other hand the shape can be controlled with great accuracy down to fairly small dimensions, of the order of micrometers or tenths of micrometers for the base of the pyramids.

By the method disclosed above a "master" for the manufacture of diamond tips is made. Of course it is not necessary to use silicon as the "master" material, but other materials are also usable. For example it is possible to use quartz as the substrate, and metals such as tungsten are also usable. The variations in the processing required for the various different substrates pertains to the field of the skilled person, such that they can easily be found by routine experimentation, and will therefore not be disclosed herein in further detail.

Figure 11:
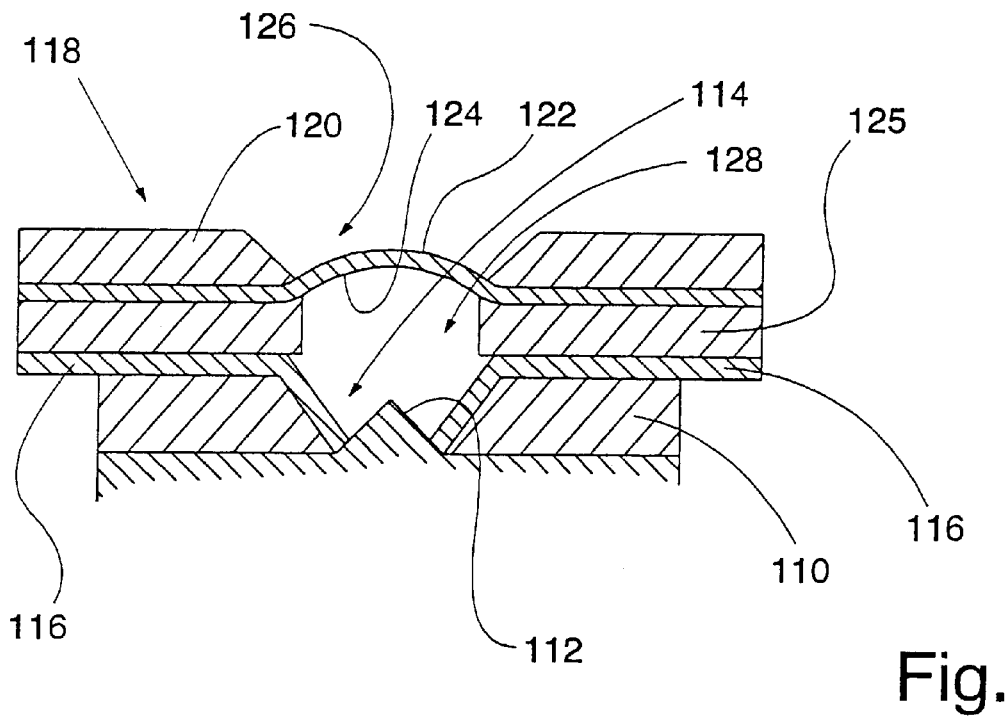
FIG. 11 shows an embodiment comprising one single pointed cathode.

In FIG. 11 there is shown an embodiment of a radiation chip having only one single tip shaped cathode in the form of a pyramid, made e.g. according to the above described method.

It comprises a base member 110 which has been provided with a diamond pyramid tip 112 using the method described above. In particular this method, i.e. the employing of micro-mechanical/microelectronic techniques, makes it possible to manufacture the desired structures in large numbers and with a high degree of accuracy. However, this structure differs slightly from the structure shown in FIG. 10g, in that the diamond tip is self-supported in the recess 114 in the base member. The recess was made by masking off that part of the base member not intended to form said recess, and etching away material all the way down to the diamond. In order to couple the diamond tip 112 to an external power source, the surface of the base member has been covered with metal to form a conductive layer 116. This layer can be used to provide a contact surface for electrical leads (not shown).

A separate cover member 118 is made by providing a substrate 120 e.g. of silicon, and depositing on the surface thereof a diamond film 122, and on the diamond film a suitable anode material may be deposited as a thin layer 124. Finally on the anode material a layer 125 of insulating material is deposited. Then an opening 126 is made by suitable masking and etching of the silicon portion 120, and a corresponding opening 128 is made through the insulating material The cover member 118 and the base member 110 are then joined to form the aggregate shown in FIG. 11. Suitable methods for joining are by using adhesive or using anodic bonding.

Figure 12:
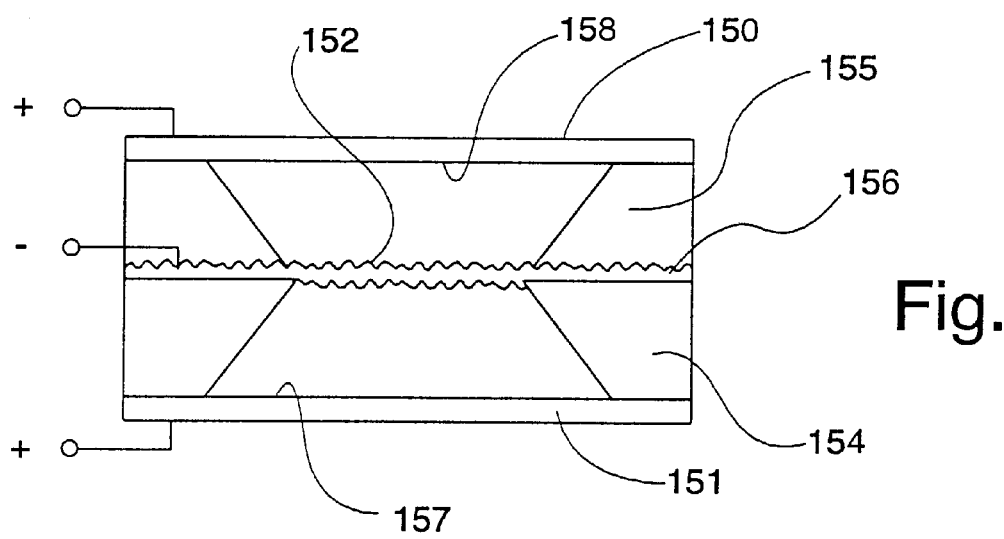
FIG. 12 shows still another embodiment comprising a double anode structure.

In FIG. 12 still another embodiment of a radiation source according to the invention is schematically shown. It comprises a double anode structure 150, 151 operating together with one single cathode 152. The cathode can be a self supporting diamond membrane 152 as shown in the figure. There are provided spacer members 154, 155 surrounding the membrane 152 for enabling a cavity to be formed on both sides of the membrane. The cavities are completed by providing a cover member 150, 151 comprising anodes 157, 158.

In order to verify the function of diamond cathodes in accordance with the invention, a series of experiments with different materials were performed.

Cathode Fabrication

Four types of cathodes were fabricated: Single tungsten tips and silicon tip arrays for comparisons and two types of polycrystalline diamond cathodes according to the invention.

The tungsten cathodes were manufactured by electro-chemical etching of 0.5 mm rods in 40 g/l NaOH (at 20 $V_{ac}$). Tip radii of approximately 2 $\mu$m were achieved.

The silicon tip arrays were defined by standard lithographic techniques and wet etched in HF:HNO$_3$:HAc (1:3:8). The silicon used was (100), n-type, and highly doped (<0.005 cm).

The diamond was grown using a hot filament chemical vapour deposition technique (HFCVD). The growth conditions were as follows: A mixture of 150 sccm H$_2$ and 1.5 sccm CH$_4$ gas, substrate temperatures around 900° C., and a chamber pressure of 50 mbar were used. The substrates were pre-treated by ultrasonic agitation with diamond seeds in C$_2$H$_5$OH for 10 minutes to pr mote diamond nucleation. During deposition the substrate temperature was monitored with a thermocouple. A 1 mm thick tungsten wire was used as a filament at 5 mm distance from the substrate. The deposition rate was about 1 $\mu$m/h. The resulting 20 $\mu$m thick diamond film was polycrystalline with a grain size of about 5 $\mu$m.

The diamond film cathodes have a doped polycrystalline diamond film on WC/Co alloy samples.

The diamond tip cathodes were manufactured by deposition of boron doped diamond on structured silicon substrates. Prior to deposition pyramidal pits were etched in the silicon substrate using 700 g/l KOH (80° C.). After deposition the silicon was sacrificially etched away in HF:HNO$_3$ (3:7) leaving diamond pyramids. The conductivity of the diamond was approximately 0.050 cm, measured using a four point probe.

Field Emission Experiments

The cathodes were assembled in a diode configuration using a silver plate or a gold needle as an anode. A well-defined cathode-anode distance was obtained by the use of mica sheets or by mounting the cathode on a micrometer screw. A current limiting resistor was included in the circuit. The emission currents were measured and shown to originate from field emission by Fowler-Nordheim plots.

The tungsten and silicon cathodes showed large fluctuations in the emission currents. Furthermore their tips degraded during use.

The highest and most stable emission currents were achieved with the diamond cathodes. The experiments were carried out at a pressure of approximately $5 \cdot 10^{-8}$ Torr. At low emission currents the fluctuation was almost ±30% but not more than around ±3% for higher currents. The voltage was increased and decreased several consecutive times with reproducible currents.

EXAMPLES

Example 1

The structure disclosed in FIG. 1 was excited by an acceleration voltage of 5 keV, yielding a field emission current of 100 pA.

Both Bremsstrahlung as well as characteristic X-rays were detected. A Cu L peak was found.

The diamond cathodes were chosen for the X-ray detection experiments. They were carried out in a scanning electron microscope (SEM) at a pressure of $7 \cdot 10^{-6}$ Torr. The radiation produced in the anode was detected with the energy dispersive X-ray spectroscopy (EDS) detector of the SEM. A wedge or tapered geometry of the anode was chosen in order to minimize X-ray absorption in the anode.

Example 2

Using a diamond film cathode the anode was placed at 100–200 $\mu$m distance from the cathode. The spectra were collected during 1000 s during which the emission current decreased substantially. Both Bremsstrahlung and peaks of characteristic radiation are visible in the spectra.

Example 3

Using a diamond tip cathode the anode was placed at 350 $\mu$m (copper) or 300 $\mu$m (gold) distance. X-ray spectra were collected during 1000 s. During acquisition the emission current fluctuated substantially.

The radiation chips disclosed above are suitable for use in radiation therapy in small vessels, such as the coronary vessels, in particular for the treatment of stenosis and restenosis. Thereby the chips are mounted at the distal end of a guide wire or a catheter, which is inserted in the body and manipulated to the location of the lesion. Normally a device of this type will be of a discardable type.

What is claimed is:

1. An X-ray source, comprising
   an anode and a cathode, said cathode comprising a homogeneous layer of an electron emitting material selected from the group consisting of polycrystalline diamond, diamond like material, amorphous diamond and diamond like carbon, said electron emitting material comprising a plurality of pointed elements; and a first support member for the cathode and a second support member for the anodes wherein said first and second support members are joined together so as to form vacuum cavity between them and such that the first and second support members are electrically insulated from each other;

said cathode and anode being disposed inside said vacuum cavity and opposite each ether, wherein at least one of said support members is comprised of diamond, and forms a self-supporting membrane.

2. An X-ray source, comprising an anode and a cathode, said cathode comprising a homogeneous layer of an electron emitting material selected from the group consisting of polycrystalline diamond, diamond like material, amorphous diamond and diamond like carbon, said electron emitting material comprising a plurality of pointed elements; and a first support member for the cathode and a second support member for the anode, wherein said first and second support members are joined together so as to form a vacuum cavity between them and such that the first and second support members are electrically insulated from each other;

said cathode and anode being disposed inside said vacuum cavity and opposite each other, wherein the material and thickness of at least one of the support members are selected to provide a filtering function for cutting off radiation of undesired energies.

3. An X-ray source, comprising an anode and a cathode, said cathode comprising a homogeneous layer of an electron emitting material selected from the group consisting of polycrystalline diamond, diamond like material, amorphous diamond and diamond like carbon, said electron emitting material comprising a plurality of pointed elements; and a first support member for the cathode and a second support member for the anode, wherein said first and second support members are joined together so as to form a vacuum cavity between them and such that the first and second support members are electrically insulated from each other;

said cathode and anode being disposed inside said vacuum cavity and opposite each other, wherein the first support member includes a layer of electron emitting material that is essentially rod shaped, and said second support member includes an anode material that is cylindrical and encloses the first support member concentrically.

4. An X-ray source, comprising an anode and a cathode, said cathode comprising a homogeneous layer of an election emitting material selected from the group consisting of polycrystalline diamond, diamond like material, amorphous diamond and diamond like carbon, said electron emitting material comprising a plurality of pointed elements; and a first support member for the cathode and a second support member for the anode, wherein said first and second support members are joined together so as to form vacuum cavity between them and such that the first and second support members are electrically insulated from each other;

said cathode and anode being disposed inside said vacuum cavity and opposite each other, wherein the second support member includes anode material that is essentially rod shaped, and said first support member includes electron emitting material that is cylindrical and encloses the first support member concentrically.

* * * * *